United States Patent [19]

Keating et al.

[11] Patent Number: 6,018,096
[45] Date of Patent: Jan. 25, 2000

[54] ANIMAL MODEL FOR ENGRAFTMENT, PROLIFERATION AND DIFFERENTIATION OF HUMAN HEMATOPOIETIC STEM CELLS

[75] Inventors: Armand Keating; Dong-dong Wu, both of Toronto, Canada

[73] Assignee: Surrogen, Inc., Vancouver

[21] Appl. No.: 08/055,105

[22] Filed: May 3, 1993

[51] Int. Cl.[7] .......................... A01N 63/00; C12N 15/00
[52] U.S. Cl. ......................... 800/2; 424/93.1; 424/93.7; 424/93.71; 435/172.3
[58] Field of Search ................................. 800/2, DIG. 5; 424/93.1, 93.7, 577, 579, 9; 435/172.3

[56] References Cited

PUBLICATIONS

Uckun et al., "Human t(1;19)(q23;p13) Pre–B Acute Lymphoblastic Leukemia In Mice With Severe Combined Immunodeficiency", *Blood*, vol. 81:3052–3062, (1993).
Vandekerckhove et al., "Thymic Selection Of The Human T Cell Receptor Vβ Repertoire in SCID–hu Mice", *J. Exp. Med.*, vol. 176:1619–1624, (1992).
Duchosal et al., "Immunization Of Hu–PBL–SCID Mice And The Rescue Of Human Monoclonal Fab Fragments Through Combinatorial Libraries", *Nature*, vol. 355:258–262, (1992).
Shah et al., "Anti–B4–Blocked Ricin Immunotoxin Shows Therapeutic Efficacy In Four Different SCID Mouse Tumor Models", *Cancer Research*, vol. 53:1360–1367, (1993).
Pisa et al., "Epstein–Barr Virus Induced Lymphoproliferative Tumors In Severe Combined Immunodeficient Mice Are Oligoclonal", *Blood*, vol. 79:173–179, (1992).
Ratajczak et al., "In vivo Treatment Of Human Leukemia In A SCID Mouse Model With c–myb Antisense Oligodeoxynucleotides", *Proc. Natl. Acad. Sci. USA*, vol. 89:11823–11827, (1992).
Moiser et al., "Resistance To Human Immunodeficiency Virus 1 Infection Of SCID Mice Reconstituted With Peripheral Blook Leukocytes From Donors Vaccinated With Vaccinia gp 160 and Recombinant gp 160", *Proc. Natl. Acad. Sci., USA*, vol. 90:2443–2447, (1993).
Carlsson et al., "Human Peripheral Blood Lymphocytes Transplanted Into SCID Mice Constitute An In vivo Culture System Exhibiting Several Parameters Found In A Normal Humoral Immune Response And Are A Source Of Immunocytes for the Production of Human Monoclonal Antibodies", *The Journal of Immunology*, vol. 148:1065–1071, (1992.
Golumbek et al., "Treatment Of Established Renal Cancer By Tumor Cells Engineered To Secrete Interleukin–4", *Science*, vol. 254:713–716, (1991).
E.K. Waller, et al., "Growth of Primary T–Cell Non–Hodgkin's Lymphomata in SCID–hu Mice: Requirement for a Human Lymphod Microenvironment", *Blood*, vol. 78, No. 10, Nov., 1991, pp. 2650–2665.
D.R. Sutherland, et al., The CD34 Antigen: Structure, Biology, and Potential Clinical Applications, *Journal of Hematotherapy*, 1:115–129, 1992, pp. 115–127.

J.W. Singer, et al., "The Human Haematopoietic Microenvironment", Recent Advances in Haematology, 1985, No. 4, pp. 1–24.
A. Keating, et al., "Effect of Different Promoters on Expression of Gene Introduced into Hematopoietic and Marrow Stromal Cells by Electroporation", Exp. Hematol., vol. 18, 1990, pp. 99–102.
R. J. Gaultieri, et al., "Identification of the Hematopoietic Growth Factors Elaborated by Bone Marrow Stromal Cells Using Antibody Neutralization Analysis", *Exp. Hematol.*, vol. 15, 1987, pp. 883–889.
D.G. Albertson, et al., "Sensivite and High Resolution in situ Hybridization to Human Chromosomes Using Biotin Labelled Probes: Assignment of the Human Thymocyte CD1 Antigen Genes to Chromosome", *The EMBO Journal*, vol. 7, No. 9, 1988, pp. 2801–2805.
S. Saeland, et al., "Effects of Recombinant Human Interleukin–3 on CD34–Enriched Normal Hematopoietic Progenitors and on Myeloblastic Leukemia Cells,", *Blood*, vol. 72, No. 5, Nov., 1988, pp. 1580–1588.
T. Lapidot, et al., "Cytokin Stimulation of Multilineage Hematopoiesis from Immature Human Cells Engrafted in SCID Mice," *Science*, vol. 255, Feb., 1992, pp. 1137–1141.
Keating, et al., "Engraftment of Donor–Derived Bone Marrow Stromal Cells", Exp. Hematol., 19:485, 1991.
E. Naparstek, et al., "Persistent Production of Colony–Stimulating Factor (CSF–1) by Cloned Bone Marrow Stromal Cell Line D2XRII After X–Irradiation", *J. of Cellular Physiology*, 126:407–413 (1986).
C. Civin, et al., "A Hematopoietic Progenitor Cell Surface Antigen Defined by a Monoclonal Antibody Raised Against KG–1a Cells", *Journal of Immunology*, vol. 133, No. 1, Jul., 1984, pp. 157–165.
R. Berenson, et al., "Antigen CD34 [+] Marrow Cells Engraft Lethally Irradiated Baboons", *J. Clin. Invest.* 81:951, (1988).

(List continued on next page.)

*Primary Examiner*—Brian R. Stanton
*Attorney, Agent, or Firm*—Foley & Lardner

[57] ABSTRACT

A chimeric, non-human, genetically-immunocompetent mammal is disclosed. The hematopoietic system of the mammal has human passaged bone marrow stromal cells and human hematopoietic stem cells obtained from a CD34[+]-enriched bone marrow fraction, and also contains transplanted syngeneic non-lymphoid spleen colony cells. The mammal may be a mouse, a rat, a rabbit, a cat, a dog, a pig, a sheep or a non-human primate. The mammal can be produced by providing a non-human, genetically-immunocompetent mammal in which its immunologic genotype comports with the norm for the species of the mammal, exposing the mammal to a level of x- or gamma-radiation that is sufficient to destroy substantially all bone marrow in the mammal to render the mammal phenotypically immunodeficient, then transplanting into the mammal syngeneic non-lymphoid spleen colony cells and human passaged bone marrow stromal cells, and transplanting into the mammal human hematopoietic stem cells obtained from a CD34[+]-enriched bone marrow fraction. Human hematopoietic cells may be obtained from the chimeric, non-human mammal.

18 Claims, No Drawings

OTHER PUBLICATIONS

Kitamura, et al., "Spleen Colny–forming Cell as Common Precursor for Tissue Mast Cells and Granulocytes," *Nature,* vol. 291, 1981, pp. 159–160.

S. Kamel–Reid, et al., "Engraftment of Immune–Deficient Mice with Human Hematopoietic Stem Cells", *Science,* vol. 242, pp. 1706–1709.

I. Lubin, et al., "Engraftment and Development of Human T and B Cells in Mice After Bone Marrow Transplantation", *Science,* vol. 252, Apr., 1991, pp. 427–431.

J.M. McCune, et al., "The SCID–hu Mouse: Murine Model for the Analysis of Human Hematolymphoid Differentiation and Function", *Science,* vol. 241, Sep., 1988, pp. 1632–1639.

D. Mosier, et al., "Transfer of a Functional Human Immune System to Mice with Severe Combined Immuno–deficiency," *Nature,* vol. 355, Sep., 1988, pp. 256–259.

K. Matthews, et al., "Bead Transfection: Rapid and Efficient Gene Transfer into Marrow Stromal and Other Adherent Mammalian Cells," *Experimental Hematology,* vol. 21, 1993, pp. 697–702.

R. Jones, et al., "Two Phases of Engraftment Established by Serial Bone Marrow Transplantation in Mice", *Blood,* vol. 73, No. 2, Feb., 1989, pp. 397–401.

T. Dexter, et al., "Stimulation of Differentiation and Proliferation of Haemopoietic Cells in Vitro", *J. Cell. Physiol.,* vol. 82, pp. 461–474.

Lord et al. "Human Philadelphia Chromosome–Positive Chronic Myeloid Leukemia: . . . ", *Exp. Hematol.,* 21:826–828 (1993).

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear -continued (ii) MOLECULE TYPE: DNA (iii) HYPOTHETICAL: NO (iv) ANTI-SENSE: NO (xi) SEQUENCE DESCRIPTION: SEQ ID NO:1:

AATCATCAAA TGGAGATTTG                                      20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:2:

GTTCAGCTCT GTGAGTGAAA                                      20

ANIMAL MODEL FOR ENGRAFTMENT, PROLIFERATION AND DIFFERENTIATION OF HUMAN HEMATOPOIETIC STEM CELLS

BACKGROUND OF THE INVENTION

Numerous studies have demonstrated the importance of in vivo animal models in the study of mammalian organ systems, especially with respect to immune systems. Unfortunately, researchers studying the human immune system have been without such a model. Recently, several groups have reported the engraftment of human bone marrow cells or human fetal liver cells into mice exhibiting severe combined immunodeficiency (SCID). Lapidot et al., *Science* 255:1137 (1992); Mosier et al., *Nature* 335:256 (1988); McCune et al., *Science* 241:1632 (1988). Another report used immunodeficient bg/nu/xid mice to achieve similar results. Kamel-Reid et al., *Science* 242:1706 (1988). None of these studies was able to establish long-term proliferation and differentiation of human tissues in the host. Additionally, transient differentiation was achieved only by the addition of exogenous human growth factors. Lethally-irradiated mice have also been used as recipients for human bone marrow cells. Lubin et al., *Science* 252:427 (1991). This study also failed to produce continued, normal human cell differentiation.

Hematopoiesis is a hierarchial process involving cells at various stages of differentiation and development. In the murine system, it is well-established that hematopoietic stem cells are capable of reconstituting the hematopoietic system of lethally-irradiated recipients. Jones et al., *Blood* 73(2):397 (1989). The most reliable assay for such activity is a transplantation assay demonstrating the reconstitution of primary and secondary recipients. Such an assay provides a valuable tool for the examination of the mouse immune system. However, because of the absence of a comparable model for humans, the understanding of human hematopoiesis is severely limited.

As mentioned above, there are reports of successful engraftment of human cells into immunodeficient mice. One of these studies, by Lapidot et al. (1992), used SCID mouse recipients for transplant of human bone marrow cells. When stimulated with combinations of erythropoietin (EPO) and human mast cell growth factor (hu-MGF), and/or PIXY321 (human IL-3 fusion protein), 76% of recipients showed engraftment of human cells in recipient bone marrow of 10 or more times that seen in animals receiving no growth factor treatment. Human tissue was of lymphoid, erythroid and myeloid character, indicating differentiation of transplanted tissue occurred. Without the addition of exogenous human growth factors, however, the relative amount of engraftment was low (0.01 to 1.0%). Moreover, it was unclear what effect extended discontinuation of growth factor treatment might have on subsequent stimulation. While this, and other previous studies represent important steps forward, they fall far short of a complete, functioning model of human hematopoiesis.

To date, however, no successful long-term engraftment, proliferation and differentiation of normal hematopoietic stem cells in a non-human mammal has been reported. As a result, no adequate animal model exists for the study of human hematopoiesis.

SUMMARY OF THE INVENTION

It is, therefore, the object of the present invention to provide a closed, non-human model for the human hematopoietic system that is complete with respect to maintenance, proliferation and differentiation of human hematopoietic tissues.

Another object of the present invention is to provide a method by which non-human mammals, capable of supporting the maintenance, proliferation and differentiation of human hematopoietic tissue without the addition exogenous factors, can be produced.

Another object of the present invention is to provide human tissue that is produced in a non-human mammal.

Another object of the present invention is to provide a method by which human tissue is produced in a non-human mammal.

In satisfying the foregoing objects, there has been provided, in accordance with one aspect of the present invention a non-human, genetically-immunocompetent mammal, the hematopoietic system of which consists essentially of cells that are of human origin, wherein some non-lymphoid hematopoietic cells are syngeneic to said mammal.

There also is provided a process for producing the non-human mammal as described above comprising the steps of (A) providing a non-human mammal in which immunologic genotype comports with the norm for the species of said mammal;

(B) exposing said mammal to a level of x- or gamma-radiation that is sufficient to destroy substantially all bone marrow of said mammal; then (C) transplanting into said mammal syngeneic spleen colony cells and human cells comprising passaged bone marrow stromal cells.

There also is provided a non-human mammal that is the product of a process comprising the steps of (A) providing a non-human mammal in which immunologic genotype comports with the norm for the species of said mammal;

(B) exposing said mammal to a level of x- or gamma-radiation that is sufficient to destroy substantially all bone marrow of said mammal; then (C) transplanting into said mammal syngeneic spleen colony cells and human cells comprising passaged bone marrow stromal cells.

DETAILED DESCRIPTION OF THE PREFERRED EMBODIMENTS

This invention provides the first closed, long-term model for human hematopoiesis in a non-human mammal, and methods for production thereof. A closed model, for the purpose of this application, is defined such that the system of interest is capable of normal function without the addition of elements exogenous to the model organism. As a result of this capability, human hematopoietic systems can be studied more effectively, not only in general, but also in individual human patients. In addition, it permits the production of human tissues for diagnosis and treatment of human disease.

The present invention demonstrates that engraftment, proliferation and differentiation of human hematopoietic stem cells can be achieved in a non-human transfer recipient. Engraftment is detected by human cell-specific colony assay. Proliferation is confirmed by the presence of committed progenitors long after transplant in the colony assay. Differentiation is confirmed by the finding of human cells of myeloid, erythroid and lymphoid nature. Active hematopoiesis is maintained without the addition of exogenous factors. And surprisingly, recipients of transplanted cells are not recognized as foreign by transferred human cells capable of such recognition.

Experiments conducted up to nine months after transfer of human cells show that both early and committed progenitor cells were maintained by recipients. Such cells could only be found in the presence of continued proliferation and maturation of the transplanted material. Therefore, these experiments, described in detail below, demonstrate the first long-term maintenance of human hematopoietic cells in significant numbers in a non-human recipient. It is also the first example of a complete, closed model of human hematopoiesis.

It is well-known that bone marrow-derived stromal cells provide a microenvironment able to support and regulate hematopoiesis in long-term bone marrow culture. Singer et al., ADVANCES IN HAEMATOLOGY, Vol. 4, pp. 1–34 (Hoffbrand, V., ed., Churchill Livingston, London, 1985); Dexter et al., J. Cell Physiol. 82:461 (1977). Investigators have reported that stromal cells regulate hematopoiesis by providing cell-cell contact as well as by producing hematopoietic cytokines. Albertson et al., EMBO 7:2801 (1988); Gualtieri et al., Exp. Hematol. 15:883 (1987); Naparstek et al., J. Cell Physiol. 126:407 (1986). As one might suspect, the lack of such factors in non-human recipients of human hematopoietic tissue markedly reduces or prevents the proliferation and differentiation of such tissues. Lapidot et al. (1992). In the present invention, this difficulty is avoided by the co-infusion of passaged stromal cells. Because these cells also successfully engraft, as reported by Wu and Keating, Exp. Hematol. 19:485 (1991), the factors necessary for proper development of human hematopoietic tissues are produced within the transfer recipient. This obviates the need for time-consuming and expensive addition of exogenous growth factors as reported elsewhere.

As will become evident, when transplanting human tissue into non-human hosts, it is highly desirable to use immunologically normal recipients. In this context, "immunologically normal" denotes an individual that displays immune system characteristics typical for the species to which the individual belongs. These characteristics would typically include, among others, functioning B-cells and T-cells as well as structural cell components, called cell surface antigens, which act as the immunologic signature for a particular organism.

Typically, the use of such immunologically normal recipients poses the following problem. The recipient's immune system, via its B- and T-cells, will identify the cell surface antigens of the engrafted tissue as foreign. This recognition leads ultimately to an immune response against the tissue, resulting in destruction or non-engraftment. This response is known as host-versus-graft rejection.

One way to circumvent host-versus-graft rejection is to use immunologically compromised recipients. Such animals exhibit two general types of deficiency, genotypic and phenotypic. Some researchers have employed genotypically-immunodeficient mice in order to circumvent this problem. These animals have genetic defects which result in the inability to generate either humoral or cell-mediated responses and include SCID mice and bg/nu/xid mice. Kamel-Reid et al. (1988); Lapidot et al. (1992). Therefore, they are unable to react against engrafted tissue. As a general proposition, however, the use of such animals is severely limited by the availability of an appropriate, immune-deficient organism as a recipient. In addition, these animals require housing in sterile environments and/or constant prophylactic antibiotic treatment.

The second category of immunodeficient recipients are those which are genetically capable of generating an immune response, yet have been phenotypically altered such that no response is seen. Typically, such phenotypically-immunodeficient recipients are generated by irradiation and this technique has been used extensively. See Jones et al. (1989). Such an approach is not without its difficulties, however. Irradiation sufficient to render the recipient incapable of mounting a response to the engrafted tissue usually results in death of the recipient due to destruction of the hematopoietic system.

The present invention obviates the need to create and/or identify genetically-immunodeficient organisms as tissue transfer recipients because immunodeficiency is achieved via irradiation of the recipient organism, and is therefore, phenotypic. Thus, any non-human mammal may be a recipient for human cells, permitting selection of the most favorable recipient, depending on the particular phenomenon to be examined. In addition, by selecting recipient organisms capable of supporting quantitatively greater human cell growth, the potential for increased human tissue proliferation is enhanced. Such non-human mammals will include, but are not limited to, mice, rats, rabbits, cats, dogs, pigs, sheep and non-human primates including baboons and chimps. It will also be unnecessary to maintain special colonies of potential recipients under sterile conditions or antibiotic maintenance.

The present invention also obviates the difficulties associated with irradiation by providing a replacement hematopoietic system following the destruction of the resident one. Specifically, by employing a set of human bone marrow stem cells capable of directing proliferation and differentiation stem cells, transfer of a stable and functioning hematopoietic system is accomplished. Thus, animals that are successfully engrafted can survive the normally lethal radiation treatment.

A second problem results when, as in the present invention, the engrafted tissues are themselves capable of mounting an immune response. Such a response is called graft-versus-host phenomenon. This effect is mediated by T-cells within the transferred cell population. Only through elaborate, expensive, and time-consuming procedures can T-cells be eliminated from the transferred cell population. Previous studies of human cells transferred into non-human hosts have not directly addressed this issue. In fact, it is unclear whether graft-versus-host reactions actually occur in SCID mice. Lapidot et al. (1992).

The present invention, by way of contrast, employs a system where one expects graft-versus-host reactions. Yet here, there is a surprising lack of immune response by the grafted human cells against the host. This suggests a fundamental difference in human T-cell development and/or function following transfer into a non-human host. Regardless of the mechanism, the absence of graft-versus-host reactions in the present invention allows the use of normal human tissues without concern for the presence of T-cell activity.

Another important aspect of the present invention is the co-infusion of human cells with syngeneic non-lymphoid spleen colony cells. These cells are known to have profound effects on hematopoietic reconstitution and, to a limited extent, exhibit hematopoietic potential. Kitamura et al., Nature 291:159 (1981).

In addition to providing the first general animal model for human hematopoiesis, the present invention permits the study of the hematopoietic system of a particular patient.

Thus, abnormal hematopoietic systems can be examined on an individual basis and compared to model systems derived from normal patients. The medical conditions which could be examined in this manner might include, but are not limited to acute and chronic leukemias of myeloid, lymphoid or multilineage cell origin, the myelodysplastic syndromes, myeloproliferative disorders, aplastic anemia, disorders involving deficiencies of single hematopoietic lineages such as pure red cell aplasia, thrombocytopenia or neutropenia and AIDS. As a result, subtle differences in both the pathology and responsiveness to treatment in a given patient can be examined outside that patient's body. The benefits of having such "custom-made" experimental vessels at the organismal level are apparent.

The present invention also provides for the use of non-human recipient organisms as "factories" for human tissues. One previous limitation in human biological and medical research has been the lack of human tissues on which to conduct research. If appropriate tissues are not available in a timely fashion, or in sufficient quantities, the ability of the investigator to conduct meaningful experiments can be impaired.

However, if small amounts of human tissue could be propagated outside the human body, the potential for producing relatively large quantities of human tissues could be realized. There have been two general approaches employed to solve this problem. The first, tissue culture of human cells in vitro, is generally limited by the mortality of cells outside the human body. The exception to this rule is the propagation of transformed cells. These cells, however, are generally not representative of normal cells and are only available on a fortuitous basis.

The other method used to produce human tissues is by grafting into non-human hosts. Yet this technology is limited by the immunologic reactions, by and against grafted tissue, described more fully above. One way to circumvent this phenomenon is to use hosts which are unable to mount an immune response to grafted tissues, such as genetically or phenotypically immunodeficient recipients. As mentioned, the use of genetically immunodeficient organisms is less than ideal due to the total immunodeficiency of the organism and the limitation as to the size and type of animal that may be used. The irradiated recipient, while circumventing these problems, faces the alternative difficulty of surviving radiation sufficient to knock out its immune function.

By practicing the present invention, one skilled in the art can overcome all the difficulties described above in the production of human tissue. Employing irradiated animals, one may select an appropriate host exhibiting any given desirable biologic characteristic. Further, repopulating the irradiated recipient with an bone marrow stem cells results in the reestablishment of both immunocompetency and hematopoiesis in the host organism, thus obviating health concerns. Thereafter, hematopoietic cells, or any other co-infused, non-hematopoietic human tissues which engraft and proliferate, can be harvested. Such non-hematopoietic cells might include, but are not limited to liver, pancreas, brain, intestine, bone and cartilage. In many cases, the irradiation and engraftment may be performed on fetuses after removal from the womb, followed by reimplantation. In this way, the recipient organism (i.e., the fetus) can be protected by the mother's immune system prior to the establishment of the transferred human immune system. In addition, it may be possible to replace entire recipient organs or organ systems with tissue derived from a single human patient, effectively creating an "ersatz" human in the non-human recipient.

Due to the complexity of the human system, it was found more instructive to initially use enriched or purified cell populations to study hematopoietic stem cells. Cell purification can be based upon the presence of the cell surface antigens mentioned previously. The CD34 antigen is one of the best-characterized human hematopoietic stem cell antigens, being expressed in 1%–3% of normal human bone marrow cells. Bone marrow cells that express CD34 include colony-forming cells of all lineages, as well as their precursors. Experiments show that the CD34+ marrow cell fraction is enriched for a variety of primitive, multipotent, and committed progenitors (Civin et al., *J. Immunol.* 133:157 (1984); Saeland et al., *Blood* 72:1580 (1988)) which, in the presence of appropriate stimuli, can differentiate into myeloid or erythroid colonies in vitro and are capable of reconstituting normal marrow function in lethally irradiated primates. Berenson et al., *J. Clin. Invest.* 81:951 (1988).

In one version of the present invention, lethally-irradiated mice are co-infused with syngeneic mouse spleen colony cells, human marrow cells enriched for the CD34+ fraction, and passaged human bone marrow stromal cells. Surviving transplant recipients are screened by PCR and found to contain human DNA sequences. Examination of transplant recipients' bone marrow cells four months after engraftment detects from 11.9 to 68.3 percent human hematopoietic progenitors using a human hematopoietic colony assay. In contrast, engraftment of human hematopoietic progenitors in transplant recipients who do not receive co-infused human marrow stromal cells is 2.9 percent or less. Confirmation of human origin of hematopoietic progenitors is established by analysis of individual colonies using PCR amplification of human X-chromosome specific sequences and corroborated by in situ hybridization of marrow cells with a human X-chromosome specific biotinylated probe. Southern blot analysis of DNA extracted from the spleen, thymus and bone marrow of the transplanted animals indicates that human cells were evenly distributed in these tissues. Transplant recipients tested nine months after co-infusion show significant numbers of mature human granulocytes, demonstrating sustained hematopoiesis of human immune cells.

The preceding paragraph underscores the importance of the inclusion of stromal cells with transplanted tissues. When transplanting non-hematopoietic tissues, other stromal cells or the relevant analogue can be used. Liver stroma (Küpfer cells, etc.) would be used when transplanting liver tissue, pancreatic stroma would be used when transplanting islet cells and microglial cells would be used when transplanting brain tissue.

The finding that stromal cells play an important role in facilitating engraftment of foreign tissues comports with other recent findings. For example, stromal cells from malignant tissues have been shown to mediate attachment, metastasis and growth in Hodgkin's and non-Hodgkin's lymphoma, breast cancer and prostate cancer.

Furthermore, human marrow stromal cells can be readily transfected with foreign genes using physical methods. Therefore, genetically modified stroma could be used to modify the recipient further. Keating et al., *Exp. Hematol.* 18:99 (1990); Matthews et al., *Exp. Hematol.* in press (1993).

In light of the preceding description, one skilled in the art can use the present invention to its fullest extent. The following examples therefore are to be construed as illustrative only and not limiting in relation to the remainder of the disclosure.

EXAMPLE 1

Human CD34+ Cell Isolation

Cells from normal human bone marrow bearing the CD34 antigen are isolated using an enrichment method which gave 99% pure CD34+ cells, according to an immunofluorescent assay as follows. Light-density mononuclear cells are isolated by Ficoll-Hypaque gradient separation at a density of 1.077 g/ml. Cells bearing the CD34 antigen are isolated from a non-adherent mononuclear fraction by positive selection using indirect immune panning with an anti-CD34 monoclonal antibody (HPCA-1; Becton-Dickinson, Mountain View, Calif.) as reported by Saeland et al., *Blood* 72:1580 (1988). A second purification step is performed using immunomagnetic beads. The CD34+ cells are resuspended at $10^7$ cells/ml with immunomagnetic beads ($10^7$ beads/ml) coated with anti-mouse immunoglobulins for 30 minutes (Dynal Inc.). The beads are removed using a magnet, and the CD34+ cells were recovered in suspension. In all experiments, the isolated cells are 95% to 99% CD34+, as judged by staining with the anti-CD34 MoAb.

EXAMPLE 2

CFU-S Assay

For co-infusion experiments with human cells, mouse spleen colonies are induced by the intravenous injection of Balb/c BM cells ($1\times10^5$/mouse) into irradiated Balb/c mice (900 cGy) as described by Till and McCulloch, *Rad. Res.* 14:213 (1961). On day 12, the nodules developed on the spleen surface are harvested and single cell suspensions are prepared.

EXAMPLE 3

Human Stromal Cell Culture

For co-infusion experiments with CD34+ cells and mouse spleen cells, human bone marrow stromal cell cultures are generated as described by Keating et al., *Blood* 64(6):1159–1162 (1984) and Keating et al., *Exp. Hemtol.* 18:99–102 (1990). Fresh human bone marrow mononuclear cells are placed into a 25 cm² tissue culture flask containing 7 ml McCoy 5A medium supplemented with 10% horse serum and 10% fetal bovine serum and $10^{-6}$ M hydrocortisone. The culture is incubated at 37° C. in a humidified atmosphere containing 5% $CO_2$ in air; once a week, half the culture medium and non-adherent cells is removed until the adherent layer became confluent. After two to three weeks, the adherent layer is removed by treatment with trypsin, recultured in the same medium, and passaged a total of 3–4 times.

EXAMPLE 4

Transplantation

In order to investigate if human CD34+ cells can be engrafted into normal murine recipients, one million such CD34+-enriched cells, the equivalent of $10^8$ bone marrow cells, were transplanted into lethally-irradiated BALB/c mice (Jackson Laboratory, Bar Harbor, Me.) in each of two groups—Groups I and II. Animals in both groups were transplanted with syngeneic mouse spleen colony cells in the amount of $3\times10^6$ per mouse in order to ensure murine hematopoietic reconstitution of the irradiated animals, but only animals in Group II received passaged human stromal cells in the amount of $1\times10^7$ cells per mouse. A total of 26 mice were transplanted with CD34+ cells and syngeneic spleen colony cells, of which 12, constituting Group II, are also transplanted with human marrow stromal cells. Of the 26 mice transplanted, 15 survived for more than four months. Eight of the 26 mice died during the first month, while three died during the 3 to 4 months after transplantation.

EXAMPLE 5

Polymerase Chain Reaction (PCR)

Four months after transplantation, peripheral blood of the recipients was collected and examined for the presence of human cells by polymerase chain reaction (PCR) analysis. Individual colonies were picked from culture dishes. After washing once with distilled water, the spleen colony cells were digested in 100 µl of buffer [containing 200 µg/ml proteinase K, 50 mmol./L Tris-chloride (pH 8.5), 1 mmol/L EDTA, and 0.5% Tween 20] at 56° C. for 1 hour with shaking. After digestion, the samples were boiled for 10 minutes to inactive proteinase K. For amplification, 5 µl of the sample was subjected to PCR amplification using 2.5 units Taq enzyme (Boehringer Mannheim, FRG), 250 ng of each primer, and 100 µmol/L of each DNTP (Boehringer) in a final reaction volume of 100 µl buffer. For the amplification of the human X alphoid repeat sequence, the primers of the sense and antisense were: 5'-AATCATCAAATGGAGATTTG-3' (SEQ ID NO: 1), 5'GTTCAGCTCTGTGAGTGAAA-3' (SEQ ID NO: 2), respectively (Witt et al., *Human Genetics* 82:271–274 (1989). Amplification was at 94° C. for 30 seconds, 54° C. for 30 seconds, and 72° C. for 1.5 minutes for 30 cycles. Amplified products were electrophoresed on 2.5% agarose (FMS) and stained by ethidium bromide. As shown in Table I, recipients in both experimental groups (with or without human stromal cells) contained human cells.

EXAMPLE 6

Colony Assay

In order to further characterize these human cells, single cell suspensions of the recipient bone marrows were plated and colony assays, optimized either for the growth of a human multilineage colony (CFU-GEMM) or mouse granulocyte-macrophage progenitors (CFU-GM), were performed:

Human CPU-GEMM. Semisolid cultures in methylcellulose are produced according to a standard method (Keating and Toor, [reference]), and modified by plating $1\times10^5$ cells per tissue culture grade 35 Petri dish, in the presence of 10% human plasma, 10% fetal bovine serum, 1–4 units/ml erythropoietin, rhSCF (CytoMed, MA) and rhIL-3 (Amersham). Duplicate dishes are plated in each experiment after 12 days of incubation at 37° C. in 5% $CO_2$ in air. The colonies are counted using an inverted phase-contrast microscope.

Murine CFU-GM. Bone marrow cells are gently dispersed into a single cell suspension in Iscove's Modified Dulbecco's Medium (IMDM) containing 10% fetal bovine serum. To measure granulocyte-macrophage colony-forming cells (CFU-GM), bone marrow cells ($1\times10^5$) are cultured in 1 ml IMDM containing 0.3% Difco agar and IL-3 (as produced from an IL-3-producing cell line provided by G. Mills, Toronto). After incubation for 7 days at 37° C. in 5% $CO_2$ in humidified air, granulocyte-macrophage colonies (CFU-GM) containing >50 cells are counted. All cultures were performed in duplicate.

Since murine IL-3 does not stimulate the growth of human hematopoietic progenitor cells, and human IL-3 has no effect on murine cells, the differing culture conditions allow a determination of cross-stimulation to be made. The results, set forth in Table II, show that no cross-stimulation was observed. Table II also contains a summary of the information gained from an analysis of colonies obtained from the marrow cells of recipient mice.

In Group II, a large proportion of early myeloid progenitors were detected under culture conditions suitable to human hematopoietic progenitors. Comparing this result to the colonies detected under culture conditions suitable for murine progenitors, the ratio of human:mouse colonies varied from 11.9% to 68.3%. In terms of colony formation, results were similar to those observed with normal human marrow controls. In contrast, the Group I recipient mice which did not receive human stromal cells contained very few human hematopoietic progenitors detected with the granulocyte-macrophage colony assay examined after 12 days in culture. No committed erythroid progenitors (BFU-E) were detected in this group.

Some of the Group II recipients were followed for 9 months after transplantation. An analysis of human hematopoietic progenitors present in the bone marrow of these recipients using an in vitro colony assay is shown in Table III. Human committed progenitors (3.8% to 23%) were found in three of the four mice. The human origin of individual colonies was confirmed by PCR analysis. The sustained maintenance of committed human hematopoietic cells in the recipient mice suggests that the engrafted CD34+ cells developed in the bone marrow of recipients and showed sustained proliferation and differentiation.

EXAMPLE 7

PCR Analysis of Individual Hematopoietic Colonies

In order to demonstrate that the colonies detected under CFU-GEMM culture conditions are indeed human hematopoietic cells, PCR is used to amplify and detect the human X chromosome α-satellite repeat in individual human multi-lineage colonies. PCR amplification of normal human DNA results in a 130 bp band (Witt and Erickson, *Human Genetics* 82:271 (1989). PCR was performed essentially as described above. To measure background amplification in the PCR assay, 100 ng of DNA from Balb/c granulocyte-macrophage colonies is used as a negative control.

The results indicate that all the colonies generated under culture conditions suitable for animal or human hematopoietic cells contained the 130 bp specific human DNA product, while no PCR amplification product was seen in the negative controls. Lane designations are as follows: lane 1, 1 kB molecular marker; lane 2, colony DNA from human male cells; lane 3, colony DNA from human female cells; lane 4, colony DNA from Balb/c mice; lanes 5–10, individual colonies from recipients transplanted with CD34+ cells, spleen colony cells and human stromal cells for 4 months. For example, for recipient #4, 10 colonies were isolated and individually analyzed (Table I); all 10 were positive for the human sequence.

EXAMPLE 8

Isolation of Genomic DNA and Southern Blot Analysis

In order to examine the tissue distribution of human hematopoietic cells in transplant recipients, Southern blot analysis is performed. Standard procedures (Maniatis et al.) for the preparation of genomic DNA samples are used. Ten µg of genomic DNA is digested with the appropriate restriction enzyme and then electrophoresed through a 0.7% agarose gel. Following Southern transfer to Hybond-N (Amersham) nylon membranes and subsequent baking, membranes are placed in a bag containing phosphate buffer prehybridization solution containing 5× SSC, 0.45% skim milk power, 0.1% SDS, pH 7.2. Blots are hybridized overnight at 42° C. using the same prehybridization solution containing 9% dextran sulfate. After hybridization, the blots are extensively washed in 2× SSC, 0.1% SDS for 20 min. at room temperature, and in 0.1× SSC, 0.2% SDS for 10–30 min. at 65° C. The autoradiograph is exposed at −70° C. using an intensifying screen.

A human Factor 1xprobe (McGraw et al., *Proc. Nat'l. Acad. Sci. USA* 82(9): 2847–2851 (1985), linear and gel purified, was labelled (>$6\times10^8$ cpm/µg DNA) with $^{32}P$ using the random primer method. All four recipients examined contained human cell DNA in thymic, splenic, and marrow tissues. DNA was extracted from recipient mice 18 weeks after engraftment with CD34+ cells. Mouse numbers correspond to those in Table II (Group II). Lane designations are as follows: HBM, normal human bone marrow; MBM, Balb/c mouse bone marrow; THY, recipient thymus; SPL, recipient spleen; BM, recipient bone marrow.

EXAMPLE 9

In Situ Hybridization

Fluorescent in situ hybridization has become an important technique for visualizing genetic material in fixed cells. A major advantage of this method is that interphase human hematopoietic cells, including immature hematopoietic cells, can be distinguished from murine cells using a human-specific probe. The in situ hybridization method can be used to further confirm the presence of human hematopoietic cells in the transplant recipients. For in situ hybridization, bone marrow cells are incubated in 75 mM KCl for 15 min. at 37° C. The cells are spun down and fixed with two changes of methanol/acetic acid (3:1 v/v). Cells are centrifuged on cleaned slides, allowed to air dry overnight, and gradually dehydrated with ethanol. Before use, slides are treated with RNase A (100 µg/ml) in 2× SSC for one hour at 37° C., with proteinase K (0.1 µg/ml in 20 mM Tris-HCl, 2 mM CaCl2, pH 7.4), for 7.5 min. at 37° C. and are post-fixed with 4% paraformaldehyde for 10 min. dehydrated, and kept at room temperature until used. DNA is denatured by immersion of the slides in 70% formamide in 2× SSC, pH 7, for two minutes at 70° C. This is followed by immersion in ice-cold 70% ethanol, and by continued dehydration with ethanol.

The probe is denatured by heating the hybridization mixture, followed by quick cooling on ice, and added to slides. After a coverslip is added and sealed with rubber cement, the slides are incubated in a moist chamber for 12 to 16 hours at 37° C. After hybridization, the slides are washed in two changes of 50% formamide, 2× SSC and in three changes of 2× SSC at 40° C. for twenty min. each.

For detection of hybridization, the slides are overlayed with 10 µl fluorescein-labelled avidin (Vector Laboratories) in 2× SSC plus 1% BSA. After incubation of 45 min. at R.T. in the dark, the slides are washed in two changes of 2× SSC, 1× SC and 0.5× SSC, for 5 min. each, and then counter-stained with propidium iodide (PI, 0.5 µg/ml) in anti-fade solution.

The probe, a human X-chromosome α-satellite DNA (Oncor Inc.) that does not hybridize with murine DNA (Waye et al., *Nucleic Acids Res.* 13(8):2731–2734 (1985)) (20 ng/µl), was added to hybridization mixture which contained 50% formamide, 2× SSC, and 500 µg/ml of carrier salmon sperm DNA. Regions to which the probe bound appear yellow, whereas the remaining DNA appears red in the microphotographs due to the superposition of green FITC-and red PI-fluorescence. The mouse numbers correspond to those in Table II (Group II). Panel A cells are normal human bond marrow cells (positive control). Panel B cells are normal Balb/c bone marrow cells (negative control). Magnification is 630×. Hybridization results indicate the presence of human hematopoietic cells in the bone marrow of murine transplant recipients and confirm results obtained with Southern blots of marrow DNA and PCR analysis of individual hematopoietic colonies.

These results are the first to show the presence of very early as well as terminally-differentiated human hematopoietic cells. Because donor human cells were enriched for early hematopoietic progenitors and lacked terminally differentiated cells, the appearance of significant numbers of mature human granulocytes as well as the detection of human multi-lineage colonies in mice reconstituted nine months previously, indicates that human donor cells not only engrafted, but proliferated and differentiated in vivo as well.

EXAMPLE 10

Analysis of Bone Marrow Cells from Murine Recipients Investigated Nine Months after Transplantation of Human CD34+ Cells and Human Passaged Marrow Stromal Cells Cell sorting experiments can determine levels of murine and human lymphoid cells in long-term reconstituted recipients. Analysis with a FACScan instrument was performed using the following monoclonal antibodies:

1. goat•anti-human IgG Fc: human B cells (affinity purified F(ab')2 preparation, mouse Ig adsorbed and FITC labeled)
2. mouse•anti-human CD3: human T cells (phycoerythrin labeled IgG2a)
3. goat•anti-mouse IgG: murine B cells (affinity purified F(ab')2 human Ig adsorbed and P-PE labeled)
4. hamster•anti-mouse CD3: murine T cells (FITC labeled IgG)

Three color sorting with biotin/streptavidin-PerCP labeled anti-CD45 (T200) antibody, recognizing human/murine and human nucleated hematopoietic cells, was used. The frequency of cells was established as follows: human B cells—9%; human T cells—12%, murine B cells 2%; murine T cells—3%.

EXAMPLE 11

PCR Analysis of Recipient Bone Marrow Cells for Human and Murine T and B Cells Nine Months after Transplantation Human/murine lymphoid subpopulations were sorted using the monoclonal antibodies as described in Example 9. The sorted subpopulations were subjected to PCR analysis for specific human and murine T and B cell sequences. PCR analysis was performed according to our modification of standard methods. Wu and Keating, (1993).

The following primers were used to detect Ig mRNA (i.e., B cell message):

sense—Igh-J primer recognizing, human and murine J regions antisense—CH1 region of murine IgG, recognizing all IgG isotypes antisense—CH2 region of human IgG, recognizing all IgG isotypes The following primers were used to detect T cell receptor mRNA:

sense—TCR β-chain-J regions recognizing, human and murine J regions antisense—CH1 region of murine TCR β-chain, recognizing all murine TCR β-chain isotypes antisense—CH2 region of human TCR β-chain, recognizing all human TCR β-chain isotypes For each set of primers, amplification was seen, thus confirming the presence of both human and murine B and T cells.

TABLE I

PCR amplification of human DNA from reconstituted Balb/c mice using human X-chromosome α repeat primers.

|  |  | Peripheral blood | Thymus | Spleen | Bone Marrow | Colonies in human CFU-GEMM assay |
|---|---|---|---|---|---|---|
| GROUP I |  |  |  |  |  |  |
| mouse | #1 | + | + | + | + | 1/1 |
|  | #2 | + | + | + | + | 1/1 |
|  | #4 | + | + | + | + | 1/2 |
| Total: |  |  |  |  |  | 3/4 |
| GROUP II |  |  |  |  |  |  |
| mouse | #1 | + | + | + | + | 7/7 |
|  | #2 | + | + | + | + | 10/10 |
|  | #3 | + | + | + | + | 10/10 |
|  | #4 | + | + | + | + | 10/10 |
|  | #5 | + | + | + | + | 10/10 |
|  | #6 | + | + | + | + | 4/4 |
| Total: |  |  |  |  |  | 51/51 |

Group I Lethally-irradiated Balb/c mice were injected with CD34+ cells and spleen colony cells.
Group II Lethally-irradiated Balb/c mice were injected with CD34+ cells, spleen colony cells, and human stromal cells.

TABLE II

Hematopoietic colonies from Balb/c bone marrow reconstituted with CD34+ cells

| | | NCC per femur | Mouse CFU-GM[a] | | Human CFU-GEMM[a] | | Human:Mouse ratio |
|---|---|---|---|---|---|---|---|
| | | $1 \times 10^6$ | $1 \times 10^5$ cells | per femur | $1 \times 10^5$ cells | per femur | |
| GROUP I[b] | | | | | | | |
| mouse | #1 | 6.3 | 78 ± 6.0 | 4914 ± 37.8 | 1 ± 0.2 | 63 ± 3.2 | 1.2% |
| | #2 | 3.9 | 71 ± 3.4 | 2769 ± 22.6 | 0.5 ± 0.2 | 18 ± 1.2 | 0.6% |
| | #3 | 5.8 | 47 ± 2.4 | 2726 ± 13.9 | 0 | — | — |
| | #4 | 8.2 | 69 ± 3.4 | 5658 ± 27.8 | 2 ± 1.0 | 164 ± 7.8 | 2.9% |
| | #5 | 4.2 | 58 ± 4.2 | 2436 ± 17.6 | 0 | — | — |
| GROUP II[c] | | | | | | | |
| mouse | #1 | 12.2 | 22 ± 3.2 | 2684 ± 24.2 | 6 ± 0.4 | 732 ± 12.1 | 27.2% |
| | #2 | 6.9 | 48 ± 2.4 | 3312 ± 34.8 | 22 ± 1.4 | 1518 ± 16.2 | 45.8% |
| | #3 | 9.4 | 28 ± 1.4 | 2632 ± 22.4 | 16 ± 2.4 | 1504 ± 12.4 | 57.1% |
| | #4 | 7.7 | 41 ± 2.2 | 3157 ± 34.4 | 28 ± 3.2 | 2156 ± 28.2 | 68.4% |
| | #5 | 14.6 | 68 ± 3.4 | 9928 ± 42.3 | 16 ± 3.7 | 1088 ± 14.2 | 23.5% |
| | #6 | 8.2 | 42 ± 2.1 | 3444 ± 26.6 | 5 ± 1.2 | 410 ± 8.4 | 11.9% |
| Control-1[d] | | 9.8 | 88 ± 4.2 | 8674 ± 35.8 | 0 | | |
| Control-2[e] | | | 0 | | 75 ± 2.4 | | |

[a]Results are the mean ± SE from duplicate.
[b]Lethally-irradiated Balb/c mice were transplanted with CD34+ cells and spleen cells.
[c]Lethally-irradiated Balb/c mice were transplanted with CD34+ cells, spleen cells, and human stromal cells.
[d]Normal Balb/c bone marrow cells were cultured for CFU-GM.
[e]Normal human bone marrow cells were cultured for CFU-GEMM.

TABLE III

CFU-GEMM from the bone marrow of Balb/c mice reconstituted with CD34+ cells, mouse spleen cells, and human marrow stromal cells

| | | NCC per femur | Mouse CFU-GM[a] | | Human CFU-GEMM[a] | | Human: Mouse % | PCR(+) (by human x primer) |
|---|---|---|---|---|---|---|---|---|
| | | $1 \times 10^6$ | $1 \times 10^5$ cells | per femur | $1 \times 10^5$ cells | per femur | | |
| mouse[b] | #1 | 1.3 | 72 ± 3.2 | 936 ± 9.6 | 11 ± 2.2 | 143 ± 8.2 | 14.5% | 5/5 |
| | #2 | 1.1 | 65 ± 1.4 | 715 ± 10.2 | 2 ± 1.4 | 22 ± 2.2 | 3.8% | 2/2 |
| | #3 | 0.5 | 78 ± 2.6 | 390 ± 6.3 | 4 ± 1.4 | 20 ± 2.1 | 5.1% | 4/4 |
| | #4 | 2.1 | 65 ± 1.8 | 1365 ± 7.4 | 15 ± 2.3 | 975 ± 4.4 | 23.0% | 10/10 |
| Control-1[c] | | 8.9 | 84 ± 3.2 | 7476 ± 18.8 | 0 | | | |
| Control-2[d] | | | 0 | | 75 ± 4.1 | | | |

[a]Results are the mean ± SE from duplicate cultures.
[b]Lethally-irradiated Balb/c mice, reconstituted by transplantation with CD34+ cells, syngeneic mouse spleen cells, and human stromal cells, were viable.
[c]Normal Balb/c bone marrow cells were cultured for CFU-GM.
[d]Normal human bone marrow cells were cultured for CFU-GEMM.

What is claimed is:

1. A chimeric, non-human, genetically-immunocompetent mammal selected from the group consisting of a mouse, a rat, a rabbit, a cat, a dog, a pig, a sheep and a non-human primate, wherein the hematopoietic system of said mammal consists essentially of human passaged bone marrow stromal cells and human hematopoietic stem cells obtained from a CD34$^+$-enriched bone marrow fraction, wherein said mammal contains transplanted syngeneic non-lymphoid spleen colony cells.

2. A chimeric, non-human mammal according to claim 1, wherein said mammal maintains human, non-hematopoietic tissues.

3. A chimeric, non-human mammal according to claim 1, wherein said mammal is a mouse.

4. A process for producing the chimeric, non-human mammal of claim 1, comprising the steps of
   (a) providing a non-human, genetically-immunocompetent mammal in which its immunologic genotype comports with the norm for the species of said mammal;
   (b) exposing said mammal to a level of x- or gamma-radiation that is sufficient to destroy substantially all bone marrow in said mammal, thereby rendering said mammal phenotypically-immunodeficient; then
   (c) transplanting into said mammal syngeneic non-lymphoid spleen colony cells and human cells comprising passaged bone narrow stromal cells; and
   (d) transplanting into said mammal human cells that consist essentially of hematopoietic stem cells obtained from a CD34$^+$-enriched bone marrow fraction,
thereby generating the non-human mammal of claim 1.

5. A process according to claim 4, wherein said hematopoietic stem cells are CD34+ cells.

6. A process according to claim 4, wherein the non-human mammal is selected from the group consisting of a mouse, a pig, a sheep, a baboon and a chimpanzee.

7. A chimeric, non-human mammal selected from the group consisting of a mouse, a rat, a rabbit, a cat, a dog, a pig, a sheep and a non-human primate that is produced by a process comprising the steps of
   (a) providing a non-human, genetically-immunocompetent mammal in which its immunologic genotype comports with the norm for the species of said mammal;
   (b) exposing said mammal to a level of x- or gamma-radiation that is sufficient to destroy substantially all bone marrow in said mammal thereby rendering said mammal phenotypically immunodeficient; then
   (c) transplanting into said mammal syngeneic non-lymphoid spleen colony cells and human cells comprising passaged bone narrow stromal cells; and
   (d) transplanting into said mammal human cells that consist essentially of hematopoietic stem cells obtained from a CD34$^+$-enriched bone marrow fraction,
thereby generating the non-human mammal of claim 1.

8. A chimeric non-human mammal according to claim 7, wherein said human hematopoietic stem cells are CD34+ cells.

9. A chimeric, non-human mammal according to claim 7, selected from the group consisting of a mouse, a pig, a sheep, a baboon and a chimpanzee.

10. A chimeric, non-human mammal according to claim 1, wherein said hematopoietic stem cells are CD34+ cells.

11. A chimeric, non-human mammal according to claim 1, selected from the group consisting of a mouse, a pig, a sheep and a non-human primate.

12. A process according to claim 4, wherein the non-human mammal is selected from the group consisting of a mouse, a pig, a sheep and a non-human primate.

13. A chimeric, non-human mammal according to claim 7, selected from the group consisting of a mouse, a pig, a sheep and a non-human primate.

14. A chimeric, non-human mammal according to claim 1, selected from the group consisting of a mouse, a pig, a sheep, a baboon and a chimpanzee.

15. A method for the production of human hematopoietic cells from a chimeric, non-human mammal comprising the steps of:

(a) providing a non-human, genetically-immunocompetent mammal in which its immunologic genotype comports with the norm for the species of said mammal;

(b) exposing said mammal to a level of x- or gamma-radiation that is sufficient to destroy substantially all bone marrow in said mammal, thereby rendering said mammal phenotypically immunodeficient; then (c) transplanting into said mammal syngeneic non-lymphoid spleen colony cells and human cells comprising passaged bone marrow stromal cells;

(d) transplanting into said mammal human cells that consist essentially of hematopoietic stem cells obtained from a $CD34^+$-enriched bone marrow fraction; and (e) harvesting human hematopoietic cells from said non-human mammal.

16. A method for the production of human hematopoietic tissue according to claim 15 wherein said cells are of lymphoid origin.

17. A method for the production of human hematopoietic tissue according to claim 15 wherein said cells are of erythroid origin.

18. A method for the production of human hematopoietic tissue according to claim 15 wherein said cells are of myeloid origin.

* * * * *